(12) United States Patent
Sumii

(10) Patent No.: US 6,700,951 B2
(45) Date of Patent: Mar. 2, 2004

(54) X-RAY FLUORESCENCE SPECTROMETER

(75) Inventor: Koushi Sumii, Takatsuki (JP)

(73) Assignee: Rigaku Industrial Corporation, Osaka (JP)

( * ) Notice: Subject to any disclaimer, the term of this patent is extended or adjusted under 35 U.S.C. 154(b) by 78 days.

(21) Appl. No.: 10/160,121

(22) Filed: Jun. 4, 2002

(65) Prior Publication Data

US 2002/0186812 A1 Dec. 12, 2002

(30) Foreign Application Priority Data

Jun. 6, 2001 (JP) ........................................ 2001-170931
Apr. 26, 2002 (JP) ........................................ 2002-126112

(51) Int. Cl.$^7$ ........................................... G01N 23/223
(52) U.S. Cl. ........................... 378/44; 378/45; 378/208; 378/195; 378/196; 378/197
(58) Field of Search ........................... 378/44, 45, 208, 378/195, 196, 197, 50, 79, 81

(56) References Cited

U.S. PATENT DOCUMENTS

| | | | | |
|---|---|---|---|---|
| 3,361,909 A | * | 1/1968 | Talas | 378/81 |
| 3,656,453 A | * | 4/1972 | Tousimis | 118/730 |
| 3,922,542 A | * | 11/1975 | Tanguy | 378/45 |
| 4,236,072 A | * | 11/1980 | Schinkel et al. | 378/83 |
| 5,257,302 A | * | 10/1993 | Narukawa | 378/45 |
| 5,528,647 A | * | 6/1996 | Anderson et al. | 378/44 |

* cited by examiner

Primary Examiner—Craig E. Church
Assistant Examiner—Jurie Yun
(74) Attorney, Agent, or Firm—Birch, Stewart, Kolasch & Birch, LLP

(57) ABSTRACT

To provide an X-ray fluorescence spectrometer of a simplified structure of a type in which a sample can be transported to an irradiating position where the sample is irradiated with primary X-rays and analysis can be achieved by positioning a target area to be measured of the sample. When an r drive means 37 drives an r drive shaft 43, a transporting function of transporting the sample 3 and a positioning function of positioning the target area in an r direction are performed. Also, aθ drive shaft 53 of a θ drive means 38 for performing the positioning function for positioning the target area in a θ direction and the r drive shaft 43 of the r drive means 37 form a dual coaxial shaft assembly.

4 Claims, 6 Drawing Sheets

X-RAY FLUORESCENCE SPECTROMETER

BACKGROUND OF THE INVENTION

1. Field of the Invention

The present invention relates to an X-ray fluorescence spectrometer of a type wherein analysis is performed by transporting a sample to be spectroscopically analyzed towards an irradiating position and positioning a target area of the transported sample at the irradiating position.

2. Description of the Prior Art

For example, the X-ray fluorescence spectrometer has been well known in the art, in which a sample mounted on a sample holder and placed on a turret together with the sample holder is transported from a delivery position, at which replacement of the sample holder is carried out, towards an rθ stage at an irradiating position where the sample is irradiated with primary X-rays, by rotation of the turret and an arbitrarily chosen minute portion of an area to be measured of the sample is analyzed after the area to be analyzed of the sample has been positioned by appropriately driving the rθ stage at the irradiating position. With this type of the X-ray fluorescence spectrometer, it is possible to implement a mapping analysis (a distribution analysis) by repeating positioning and measurement to analyze a plurality of minute portions. Conversely, if averaged data are desired to be secured while a problem associated with non-uniformity of the sample is avoided, it is possible to achieve analysis of a round-shaped or ring-shaped target area by utilizing a so-called spinning function to continuously rotate the rθ stage at the irradiating position during measurement.

However, separate from a rotary turret that is a transport means, there is employed an rθ stage that is a positioning means. In other words, since the rotary turret that performs a transport function for transporting the sample, the r stage that performs a positioning function for positioning the target area in an r direction and the θ stage that performs a positioning function for positioning the target area in a θ direction are separately employed, the spectrometer is bulky and complicated in structure, resulting in increase of the cost.

SUMMARY OF THE INVENTION

Accordingly, the present invention has been devised with a view to the foregoing problems and is intended to provide an improved X-ray fluorescence spectrometer of a simplified structure of the type wherein analysis can be performed by transporting a sample to be spectroscopically analyzed towards an irradiating position and positioning a target area of the transported sample at the irradiating position an X-ray fluorescence spectrometer of a simplified structure of a type in which In order to accomplish the foregoing object, the X-ray fluorescence spectrometer of the present invention includes an r drive means and a θ drive means. The r drive means is operable to drive an r drive shaft to transport a sample holder in a circumferential direction about the r drive shaft between an irradiating position, at which the sample mounted in a sample holder is irradiated with the primary X-rays, and a delivery position at which replacement of the sample holder takes place and, also, for driving the r drive shaft at the irradiating position to thereby position a target area to be analyzed of the sample in the circumferential direction. The θ drive means has a function of driving a θ drive shaft at the irradiating position to continuously rotating the sample holder about a center axis thereof and operable to drive the θ drive shaft at the irradiating position to position the target area of the sample about the center axis. The r drive shaft and the θ drive shaft form a dual coaxial shaft assembly.

With the X-ray fluorescence spectrometer according to the present invention, when the r drive means drives the r drive shaft, both of the transport function of transporting the sample and the positioning function of positioning the target area in the r direction can be performed. Moreover, the θ drive shaft of the θ drive means performing the function of positioning the target area in the θ direction and the r drive shaft of the r drive means form a dual coaxial shaft assembly. Accordingly, the spectrometer can be assembled compact in structure, resulting in reduction of the cost. Also, as is the case with the θ stage employed in the conventional spectrometer, the θ drive means has a spinning function of continuously rotating the sample at the irradiating position.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE EMBODIMENTS

Figure 1:
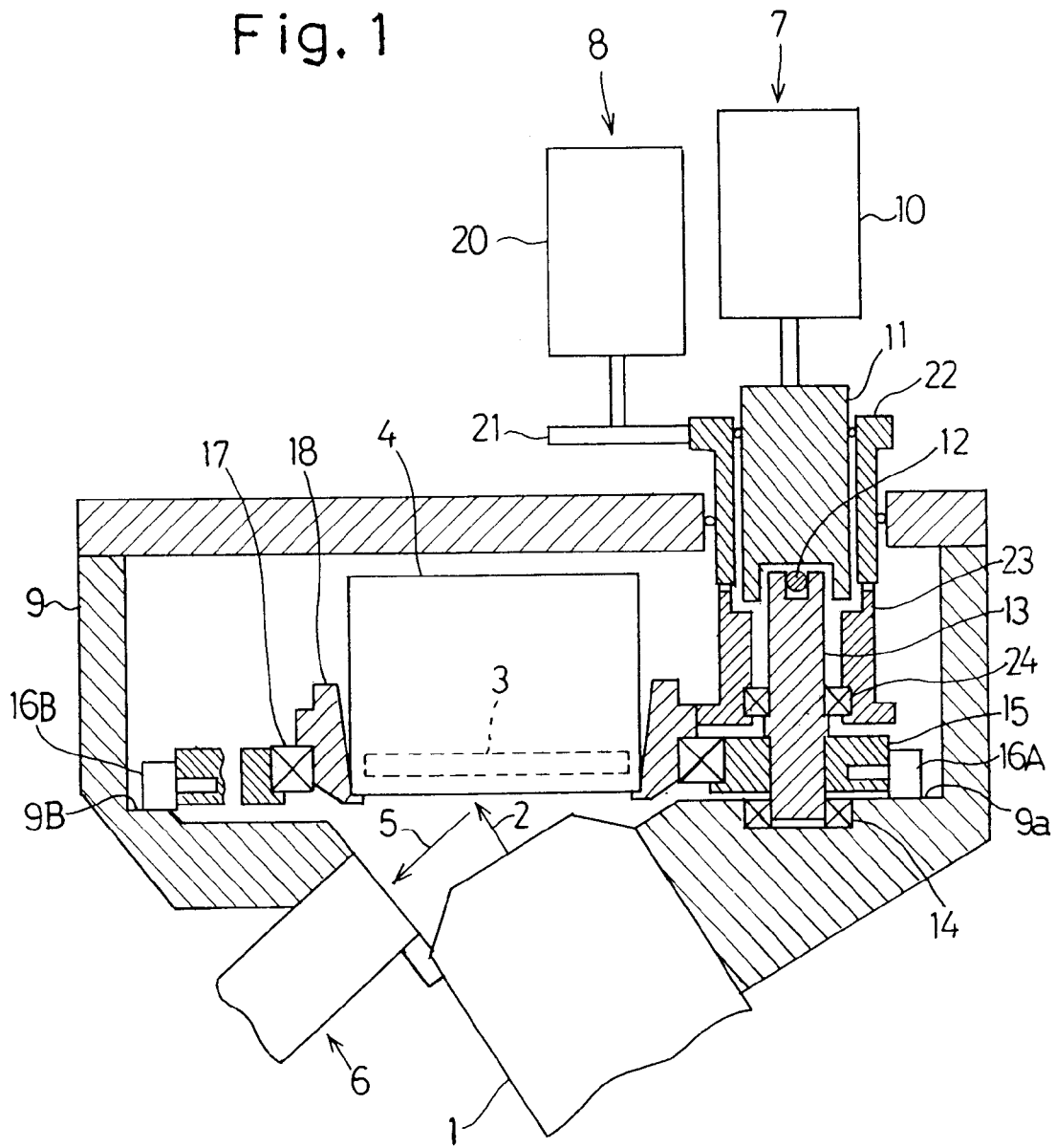
FIG. 1 is a longitudinal sectional view showing an X-ray fluorescence spectrometer of a upward-irradiating type according to a first preferred embodiment of the present invention.

Hereinafter, the structure of the X-ray fluorescence spectrometer according to a first preferred embodiment of the present invention will be described. As shown in a longitudinal sectional view in FIG. 1, the X-ray fluorescence spectrometer shown therein is of a upward-irradiating type in which a sample 3 placed within an evacuated chamber 9 is irradiated from below with primary X-rays 2 projected from an X-ray source 1 such as an X-ray tube so that the sample 3 can be excited to emit secondary X-rays 5, the intensity of which is detected and measured by a detecting means 6. Although the detecting means 6 includes a divergence Soller slit, a spectroscopic device, a light receiving Soller slit and a detector, only the divergence Soller slit is shown. It is to be noted that where the detector having a high energy resolving power such as, for example, SSD is employed, the use of the spectroscopic device is not necessary. Also, the present invention is not always limited to the X-ray fluorescence spectrometer of the upward irradiating type, but may be equally applied to the X-ray fluorescence spectrometer of a downward irradiating type in which the sample is irradiated with the primary X-rays from top.

Figure 2:
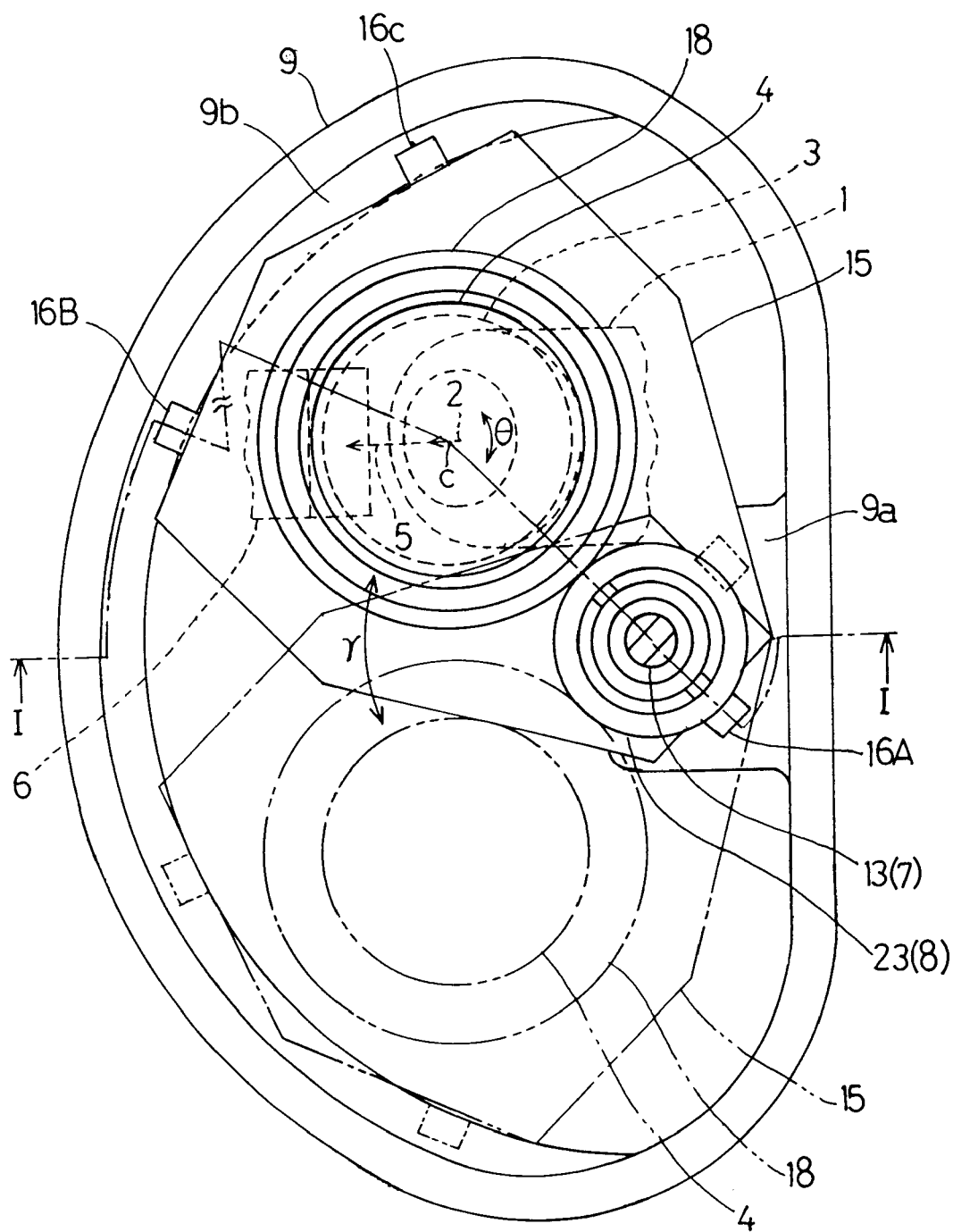
FIG. 2 is a plan view showing interior components within a chamber of the X-ray fluorescence spectrometer shown in FIG. 1.

The illustrated spectrometer includes an r drive means 7 and a θ drive means 8. As shown in a plan view in FIG. 2 showing interior components within the chamber 9, the r drive means 7 is operable to drive an r drive shaft 13 to transport the sample 3, mounted on a sample holder 4, between an irradiating position, at which the sample is irradiated with primary X-rays 2 projected from the X-ray source 1 (i.e., the position where the sample holder 4 is shown by the solid line at an upper portion of FIG. 2), and a delivery position, at which replacement of the sample holder 4 takes place (i.e., the position where the sample holder 4 is shown by the double-dotted lines at a lower portion of FIG. 2), in a circumferential direction r about the r drive shaft 13 and, also, operable to drive the r drive shaft 13 at the irradiating position to position a target area to be measured of the sample 3 in the circumferential direction r.

More specifically, as shown in FIG. 1, the r drive means 7 includes an r drive motor 10 in the form of a stepper motor having a drive shaft, a columnar r drive element 11 coupled with the drive shaft of the r drive motor 10, a pin 12 coupled diametrically with a cylindrical lower end of the r drive element 11, the columnar r drive shaft 13 having an upper end formed with a groove, in which the pin 12 is engaged, and a lower end supported by the chamber 9 through a bearing 14, a horizontally lying plate-like stage 15 coupled with a lower portion of the r drive shaft 13, and holder receptacle 18 mounted on the stage 15 through a bearing 17 and on which the sample holder 4 is placed. The stage 15 carries a plurality of, for example, three, wheel-shaped bearings 16A, 16B and 16C each having a shaft threaded to a respective portion of a perimeter of the stage 15 as shown in FIG. 2, so that the bearings 16A, 16B and 16C can roll on guide surfaces 9a and 9b formed on a bottom of the chamber 9, accompanied by rotation of the stage 15 in the circumferential direction r about the r drive shaft 13.

The θ drive means 8 has a function of driving a θ drive shaft 23 at the irradiating position to rotate continuously the sample holder 4 about its center axis C (in a θ direction) and is also operable to rotate the θ drive shaft 23 at the irradiating position to position the target area of the sample 3 about the center axis C. More specifically, the θ drive means 8 includes a θ drive motor 20 in the form of a stepper motor having a drive shaft, a θ drive gear 21 coupled with the drive shaft of the θ drive motor 20, a θ drive element 22 of a cylindrical configuration having an upper outer peripheral portion thereof meshed with the θ drive gear 21, a cylindrical θ drive shaft 23 having an upper end formed with a groove, in which a projection at a lower end of the θ drive element 22 is engaged, and a lower end rotatable relative to an inner r drive shaft 13 through a bearing 24, and a gear formed on an outer periphery of the lower end, and the holder receptacle 18 having an outer periphery meshed with the gear of the θ drive shaft 23. The r drive shaft 13 extends within the θ drive shaft 23 and, hence, the r drive shaft 13 and the θ drive shaft 23 form a dual coaxial shaft.

Each of the r and θ drive motors 10 and 20 may be of any type provided that the angular position thereof can be detected and can therefore be employed in the form of a servo motor, other than the stepper motor referred to hereinabove. A combination of a drive motor that the angular position thereof can not be detected with an encoder for detection of the angular position of the drive motor may be equally employed for each of the r and θ drive motors 10 and 20. It is to be noted that a gap between the r drive element 11 and the θ drive element 22 and a gap between the θ drive element 22 and a top (a lid) of the chamber 9 are both properly sealed. It is also to be noted that in FIG. 2, so far as the r drive means 7 is concerned, only a lower portion of the r drive shaft 13 is shown while so far as the θ drive means 8 is concerned, only a lower portion of the θ drive shaft 23 is shown. While FIG. 1 is a cross-sectional view taken along the line I—I in FIG. 2, so far as a lower portion of the chamber 9 below the bottom thereof is concerned, it is shown in section as viewed from below in FIG. 2.

The operation of the spectrometer of the structure described above will now be described. At the outset, using an input means such as, for example, a keyboard that is not shown, one or more desired area to be measured in the coordinate system of a surface of the sample 3 with its center taken as the point of origin is specified. Then, the top of the chamber 9 is opened so that the sample holder 4 having the sample 3 mounted thereon is, as shown by the double dotted line in a lower portion of FIG. 2, placed on the holder receptacle 18 that held at the delivery position (at this time the sample holder 4 is held at a predetermined angular position with respect to the θ direction), followed by closure of the top of the chamber 9. The closed chamber 9 is subsequently evacuated by means of, for example, a vacuum pump (not shown).

Thereafter, a control means having the previously mentioned input means therein causes the r drive motor 10 of the r drive means 7 to be driven a predetermined angle, for example, 90° to thereby transport the sample holder 4 towards the irradiating position (with the sample holder 4 held as shown by the solid line in the upper portion of FIG. 2). It is to be noted that the irradiating position referred to above is the position at which the sample 3 mounted in the sample holder 4 can be irradiated with the primary X-rays 2 projected from the X-ray source 1 and has a certain range. Thus, the position of the sample holder 4 as transported thereto is one of positions within this range that can be used as a reference position.

The control means then causes the r drive motor 10 of the r drive means 7 and the θ drive motor 20 of the θ drive means 8 to be driven properly to thereby position the area to be measured in the circumferential direction r and also in the θ direction so that the primary X-rays 2 from the X-ray source 1 can impinge upon the specified area to be measured and, also, the secondary X-rays 5 emitted from the specified area to be measured can be received and detected by the detecting means 6. In this way, the area to be measured can be irradiated by the primary X-rays 2 and the intensity of the secondary X-rays 2 emanating from the area to be measured can subsequently be detected and measured by the detecting means 6 to thereby accomplish the fluorescent X-ray analysis. Where a plurality of areas to be measured are specified, positioning and intensity measurements are sequentially performed to accomplish a distributive analysis.

It is to be noted that if averaged data are desired while a problem associated with non-uniformity of the sample is avoided, it is possible to achieve analysis of a round-shaped or ring-shaped large target area by utilizing the spinning function of the θ drive means 8 to continuously rotate the sample holder 4 at the irradiating position without any positioning as described above being performed.

After the measurement of the intensity with respect to the delivered sample 3 has been completely finished, the control means causes the r drive motor 10 of the r drive means 7 to rotate properly to thereby transport the sample holder 4 towards the delivery position (with the sample holder 4 held as shown by the double-dotted lines in the lower portion of FIG. 2). The top of the chamber 9 is subsequently opened in readiness for removal of the sample holder 4. In this way, the analysis work completes. However, if there is any sample 3 desired to be subsequently analyzed, the sample holder 3 having such sample 3 mounted therein is delivered, followed by repetition of the above described procedures.

According to the foregoing first preferred embodiment of the present invention, when the r drive means 7 drives the r drive shaft 13, both of a transport function of transporting the sample 3 and a positioning function of positioning the target area in the r direction can be performed. Moreover, the θ drive shaft 23 of the θ drive means 8 that performs the positioning function of positioning the target area in the θ direction and the r drive shaft 13 of the r drive means 7 are positioned coaxially one inside the other to thereby form the dual coaxial shaft. Accordingly, the spectrometer can be assembled compact in size, resulting in reduction in cost. Also, as is the case with the θ stage employed in the conventional spectrometer, the θ drive means 8 has a spinning function of continuously rotating the sample 3 at the irradiating position.

In the following description, the structure of the spectrometer according to a second preferred embodiment of the present invention will be described. As shown in a longitudinal sectional view in FIG. 3, as is the case with the spectrometer according to the previously described first embodiment, the spectrometer shown therein is of a upward-irradiating type in which a sample 3 placed within an evacuated chamber 39 is irradiated from below with primary X-rays 2, but differs from the previously described spectrometer in that in the second embodiment two sample holders 34A and 34B are adapted to be mounted on a rotating stage 45.

Figure 3:
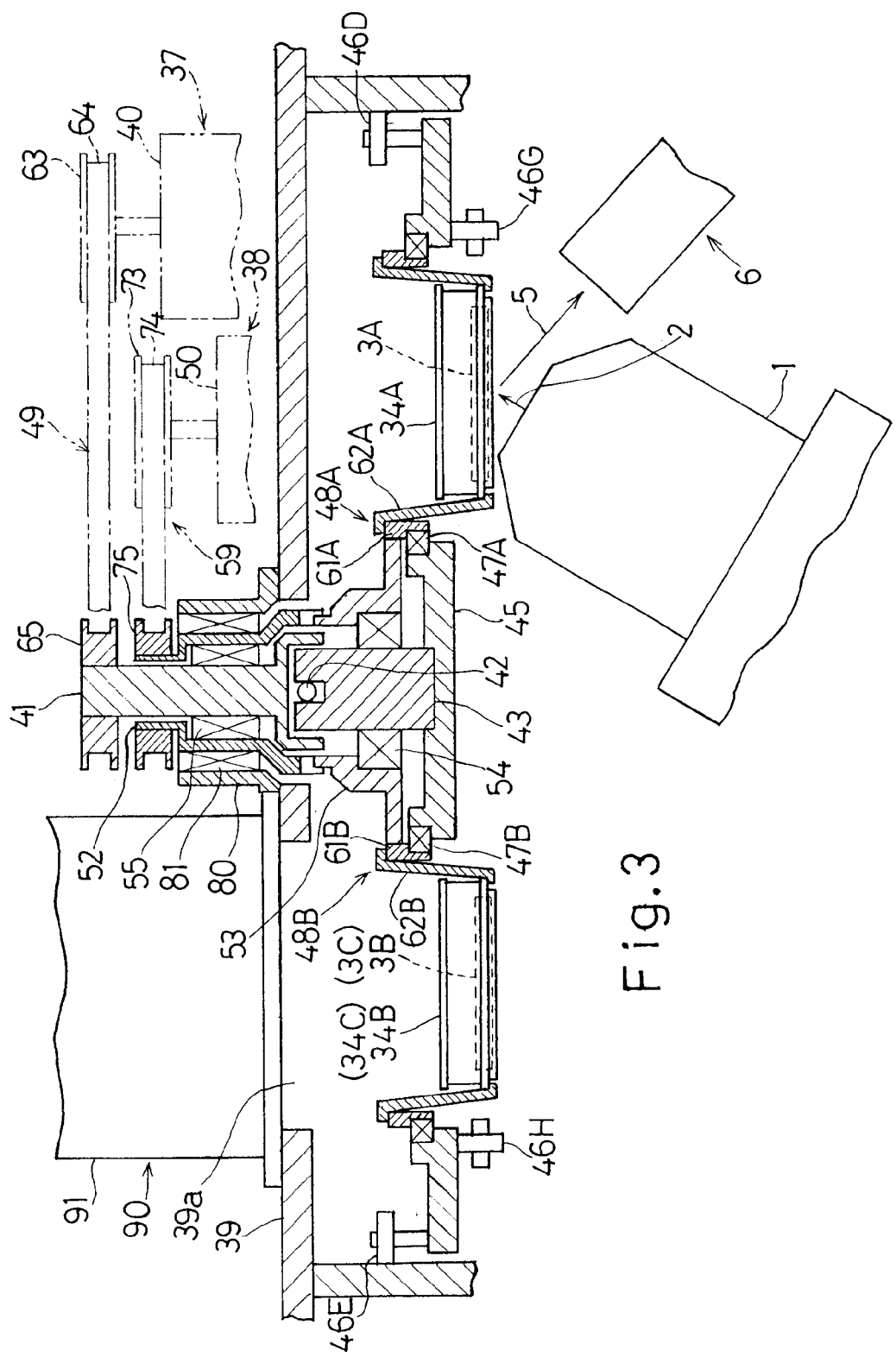
FIG. 3 is a longitudinal sectional view showing the X-ray fluorescence spectrometer of the upward-irradiating type according to a second preferred embodiment of the present invention.

The X-ray fluorescence spectrometer shown in FIG. 3 includes an r drive means 37 and a θ drive means 38. As shown in a perspective view with the chamber 39 removed in FIG. 4, the r drive means 37 is operable to drive an r drive shaft 43 (FIG. 3) to transport the samples 34A and 34B between an irradiating position (on a right side in FIGS. 3 and 4), at which the sample 3A mounted in the sample holder 34A is irradiated with primary X-rays 2 projected from the X-ray source 1, and a delivery position (on a left side in FIGS. 3 and 4), at which replacement of the sample holder 34B takes place, in a circumferential direction r about the r drive shaft 43 and, also, operable to drive the r drive shaft 43 at the irradiating position to position a target area to be measured of the sample 3A in the circumferential direction r.

Figure 4:
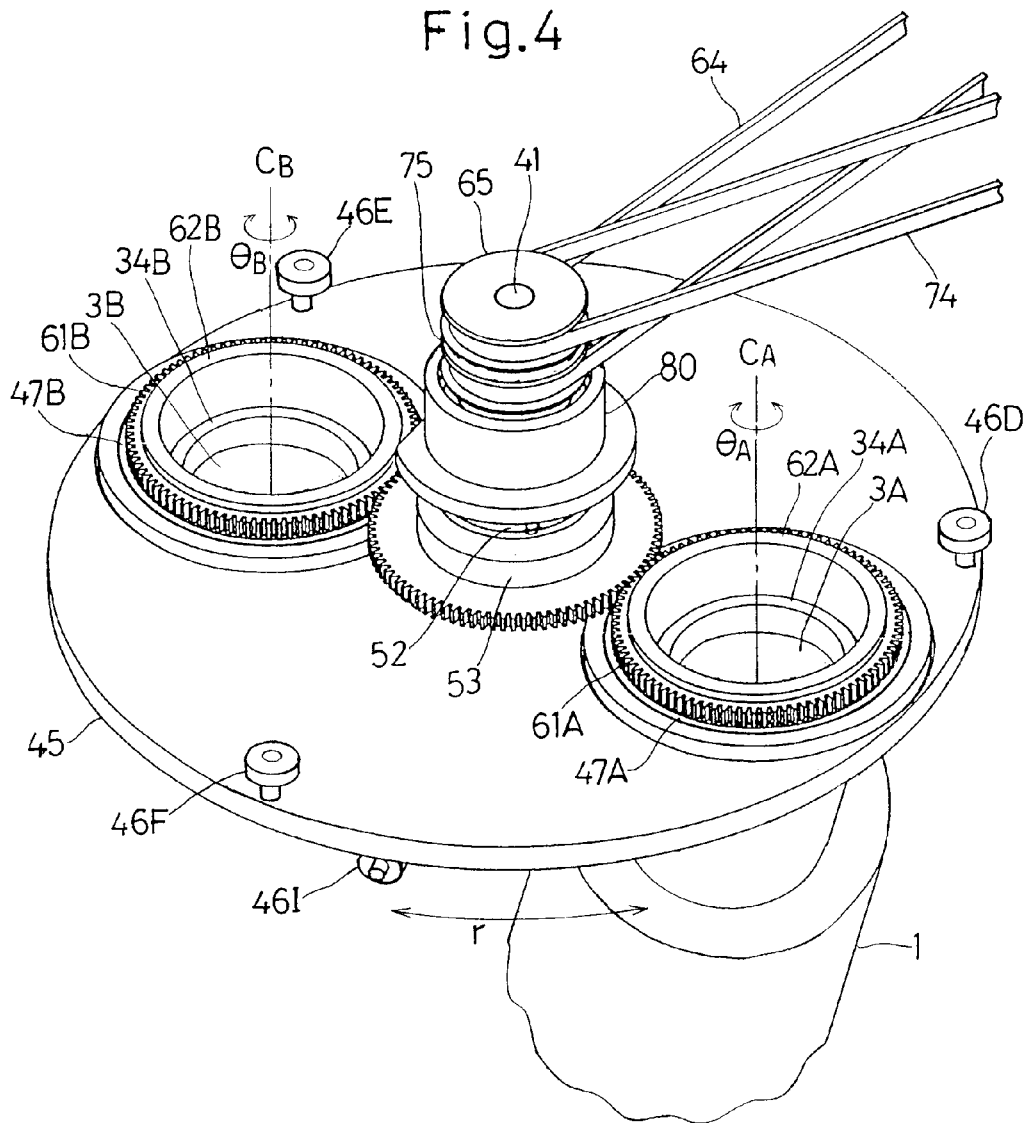
FIG. 4 is a perspective view, with the chamber removed, of the X-ray fluorescence spectrometer shown in FIG. 3.

More specifically, as shown in FIG. 3, the r drive means 37 includes an r drive motor 40 in the form of a stepper motor having a drive shaft, a columnar r drive element 41 coupled with the drive shaft of the r drive motor 40 through a transmission element 49, a pin 42 coupled diametrically (i.e., in a direction perpendicular to the plane or the sheet of FIG. 3) with a cylindrical lower end of the r drive element 41, the columnar r drive shaft 43 having an upper end formed with a groove, in which the pin 42 is engaged, a horizontally lying disc-shaped stage 45 coupled with a lower end of the r drive shaft 43, and holder receptacles 48A and 48B mounted on the stage 45 through respective bearings 47A and 47B and adapted to receive therein associated sample holders 34A and 34B. The two holder receptacles 48A and 48B are positioned spaced 180° circumferentially in the circumferential direction r (FIG. 4). The transmission element 49 includes a pulley 63 coupled with the drive shaft of the r drive motor 40, a pulley 65 coupled with the r drive element 41 utilized as a rotary shaft, and a belt 64 trained between those pulleys 63 and 65.

The holder receptacles 48A and 48B each include a wheel-shaped gear 61A or 61B fitted to the stage 45 through a respective bearing 47A or 47B, and a cup-shaped holder receptacle body 62A or 62B mounted on the associated wheel-shaped gear 61A or 61B. A step or collar is formed on a outer periphery of an upper end of each of the wheel-shaped gears 61A and 61B, and an upper outer periphery of each of the holder receptacle bodies 62A and 62B is inserted and received in an upper inner periphery of the associated wheel-shaped gear 61A or 61B. Each of the holder receptacle bodies 62A and 62B has its bottom opening downwardly while leaving an outer peripheral edge portion thereof, and the respective sample holder 34A or 34B can be placed thereon with a lower step formed in a lower outer periphery of such sample holder 34A or 34B inserted and received in a bottom inner portion thereof. Although each of the sample holders 34A and 34B is in the form of a hollow cylinder having a bottom, the bottom is opened while leaving a peripheral edge portion of a bottom plate and the respective disc-shaped sample 3A or 3B is adapted to be mounted inside the bottom thereof with its outer peripheral portions inserted and received therein, so that the primary X-rays 2 can impinge upon an undersurface of the sample 3A through the opening at the bottom of the respective sample holder 34A or 34B. It is to be noted that each of the sample holders 34A and 34B has an outer periphery of an upper end thereof that is formed with an upper step.

The stage 45 carries three, previously described wheel-shaped bearings 46D, 46E and 46F each having a shaft threaded to a respective portion of a perimeter of an upper surface of the stage 45 as shown in FIG. 4, so that respective outer peripheries of the bearings 46D, 46E and 46F can roll on an inner surface of a cylindrical wall of the chamber 39 in FIG.3. Also, so that respective outer peripheries of bearings 46G, 46H and 46I (of which the bearings 46G and 46H are shown in FIG. 3 and the bearing 46I is shown in FIG. 4) can roll on an outer peripheral portion of an undersurface of the stage 45, respective shafts of those bearings 46G, 46H and 46I are set to extend horizontally and are connected fixedly to the chamber 39 (it being to be noted that the manner in which the bearing shafts are connected is not shown). With a support structure in which those bearings 46D, 46E, 46F, 46G, 46H and 46I are utilized, the stage 45 can be rotatable in the circumferential direction r about the r drive shaft 43.

As shown in FIG. 4, the θ drive means 38 has a function of driving a θ drive shaft 53 at the irradiating position to rotate continuously the sample holder 34A about its center axis $C_A$ (in a $θ_A$ direction) and is also operable to rotate the θ drive shaft 53 at the irradiating position to position the target area of the sample 3A about the center axis $C_A$ (in the $θ_A$ direction).

More specifically, as shown in FIG. 3, the θ drive means 38 includes a θ drive motor 50 in the form of a stepper motor having a drive shaft, a stepped cylindrical θ drive gear 52 coupled with the drive shaft of the θ drive motor 50 through a transmission element 59 and rotatable relative to the r drive element 41 positioned inside thereof through a bearing 55 at an intermediate portion thereof, a cylindrical θ drive element 53 having an upper outer end formed with a projection, with which a groove at a lower end of the θ drive element 52 is engaged, and rotatable relative to the r drive shaft 43 positioned inside thereof through a bearing 54 at a lower end thereof, and the holder receptacles 48A and 48B each having its outer periphery meshed with a respective gears mounted on an outer periphery of a lower end of the θ drive shaft 53. The chamber 39 has a top (a top plate) thereof on which a cylindrical covering 80 is mounted, and the θ drive element 52 positioned inside the covering 80 is rotatable relative to the covering 80 through a bearing 81 at an intermediate portion thereof. The r drive shaft 43 extends inside and through the θ drive shaft 53 and, hence, those shafts 43 and 53 define a dual coaxial shaft. The transmission 59 includes a pulley 73 coupled with the drive shaft of the θ drive motor 50, a pulley 75 coupled with the θ drive element 52 utilized as a rotary shaft, and a belt 74 trained between those pulleys 73 and 75.

Each of the r and θ drive motors 40 and 50 may be of any type provided that the angular position thereof can be detected and can therefore be employed in the form of a servo motor, other than the stepper motor referred to hereinabove. A combination of a drive motor that the angular position thereof can not be detected with an encoder for detection of the angular position of the drive motor may be equally employed for each of the r and θ drive motors 40 and 50. It is to be noted that a gap between the r drive element 41 and the θ drive element 52, a gap between the θ drive element 52 and the covering 80, and a gap between the covering 80 and the top (the top plate) of the chamber 39 are all properly sealed. It is also to be noted that, although FIG. 3 is a longitudinal sectional representation of what is shown in FIG. 4, so far as an outer peripheral portion of the stage 45 and the chamber 39 are concerned, it shows the sectional representation taken across respective shafts of the bearings 46D, 46E, 46G and 46H are shown.

Figure 5:
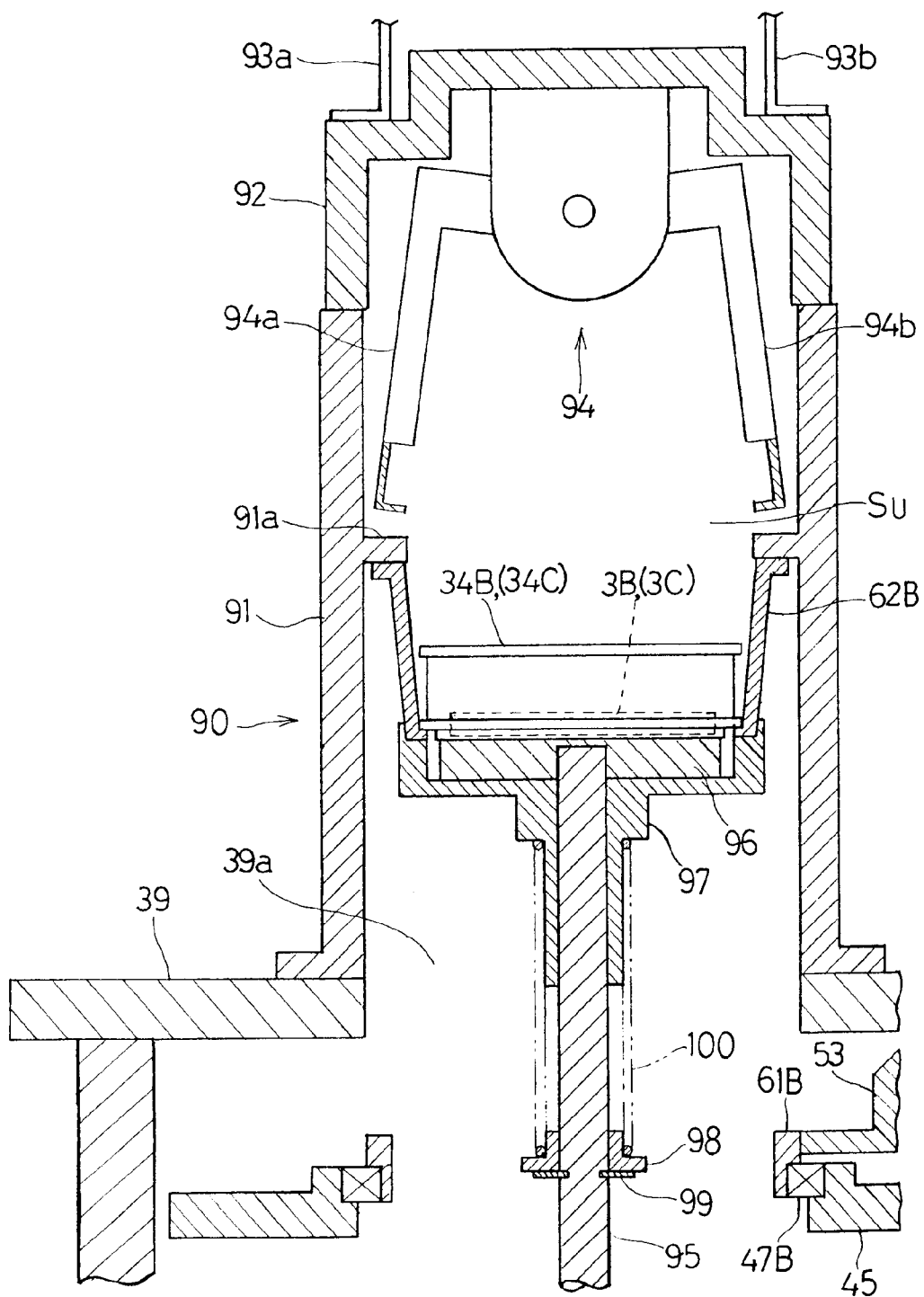
FIG. 5 is a longitudinal sectional view showing a sample replacement mechanism employed in the X-ray fluorescence spectrometer shown in FIG. 3.

The X-ray fluorescence spectrometer according to the second embodiment also includes a sample replacement means 90 of the structure, which will now be described, for facilitating replacement of the sample holder 34B and, hence, the sample 3B at the delivery position. In order for the sample holders 34B and the holder receptacle body 62B to be moved upwardly as shown in FIG. 5, the chamber 39 has its upper portion formed with an opening 39a, and a cylindrical replacement shroud 91 is mounted on an upper surface of the chamber 39 in communication with the interior of the chamber 39 through the opening 39a. A cap 92 adapted to tightly close an upper open end of the replacement shroud 91 is adapted to be moved in a horizontal direction and also in a vertical direction by means of a shifting mechanism (not shown) through a pair of stays 93a and 93b. A gripper 94 including a pair of gripping pawls 94a and 94b for selectively holding and releasing the sample holder 34B are disposed within the interior of the cap 92.

A columnar replacement shaft 95 is provided for movement up and down along a longitudinal axis of the replacement shroud 91, and a disc-shaped holder table 96 on which the sample holder 34B is placed is fixedly mounted on an upper end of the replacement shaft 95. A holder receptacle support 97 is externally slidably mounted on the replacement shaft 95 so as to form a dual relatively slidable coaxial shaft assembly. This holder receptacle support 97 has an upper portions formed to provide a cylindrical cup delimited by a cylindrical wall and a bottom wall. An upper end of the cylindrical wall of the cylindrical cup in the holder receptacle support 97 has an inner peripheral edge so recessed inwardly that when the holder receptacle body 62B is placed on the holder receptacle support 97, an outer peripheral edge of the bottom of the holder receptacle body 62B can be coaxially seated. A cylindrical stepped spring seat 98 is mounted on the replacement shaft 95 at a location below the holder receptacle support 97 and is held fixedly in position by means of a stop ring 99 engaged in a groove on the replacement shaft 95 to thereby avoid any possible downward shift of the spring seat 98. A coil spring 100 interposed between the holder receptacle support 97 and the spring seat 98 exerts a biasing force with which the holder receptacle support 97 can be urged upwardly relative to the replacement shaft 95 at all times with the undersurface of the holder table 96 consequently held in contact with an inner surface of the bottom of the holder receptacle support 97.

It is to be noted that the replacement shroud 91 has an inner surface formed with a step 91a to which the upper end of the holder receptacle body 62B then placed on the holder receptacle support 97 is engaged from below. It is also to be noted that a gap between the cap 92 and the replacement shroud 91, a gap between the replacement shroud 91 and the chamber 39, the step in the replacement shroud 91 and the holder receptacle body 62B, a gap between the holder receptacle body 62B and the holder receptacle support 97 and a gap between the holder receptacle support 97 and the replacement shaft 95 are all sealed properly.

The operation of the spectrometer of the structure described above in accordance with the second embodiment of the present invention will now be described. This operation is automatically performed by a control means not shown. It is assumed that in FIG. 3 the sample holder 34A is in a condition immediately after having been transported to the irradiating position, but prior to the target area of the sample 3A being positioned and, accordingly, the sample holder 34A is held at the reference position that is one of the positions within the range as hereinbefore described in connection with the previous embodiment. On the other hand, when the sample holder 34A is thus held at this position, the other sample holder 34B is held at the delivery position with the sample 3B thereon having been subjected to the intensity measurement at the irradiating position. At this time, as shown in FIG. 5, the holder table 96 and the holder receptacle support 97 are, together with the replacement shaft 95, elevated from below the sample holder 34B and the holder receptacle body 62B then held at the delivery position and the sample holder 34B and the holder receptacle body 62B are consequently pushed upwardly while resting on the holder table 96 and the holder receptacle support 97, until the upper end of the holder receptacle body 62B is brought into engagement with an undersurface of the step 91a in the replacement shroud 91. As a result thereof, a space $S_U$ defined by the interior of the cap 92 and the interior of the replacement shroud 91 above the holder receptacle body 62B and the holder receptacle support 97 is thus hermetically sealed and isolated from the interior of the chamber 39.

Figure 6:
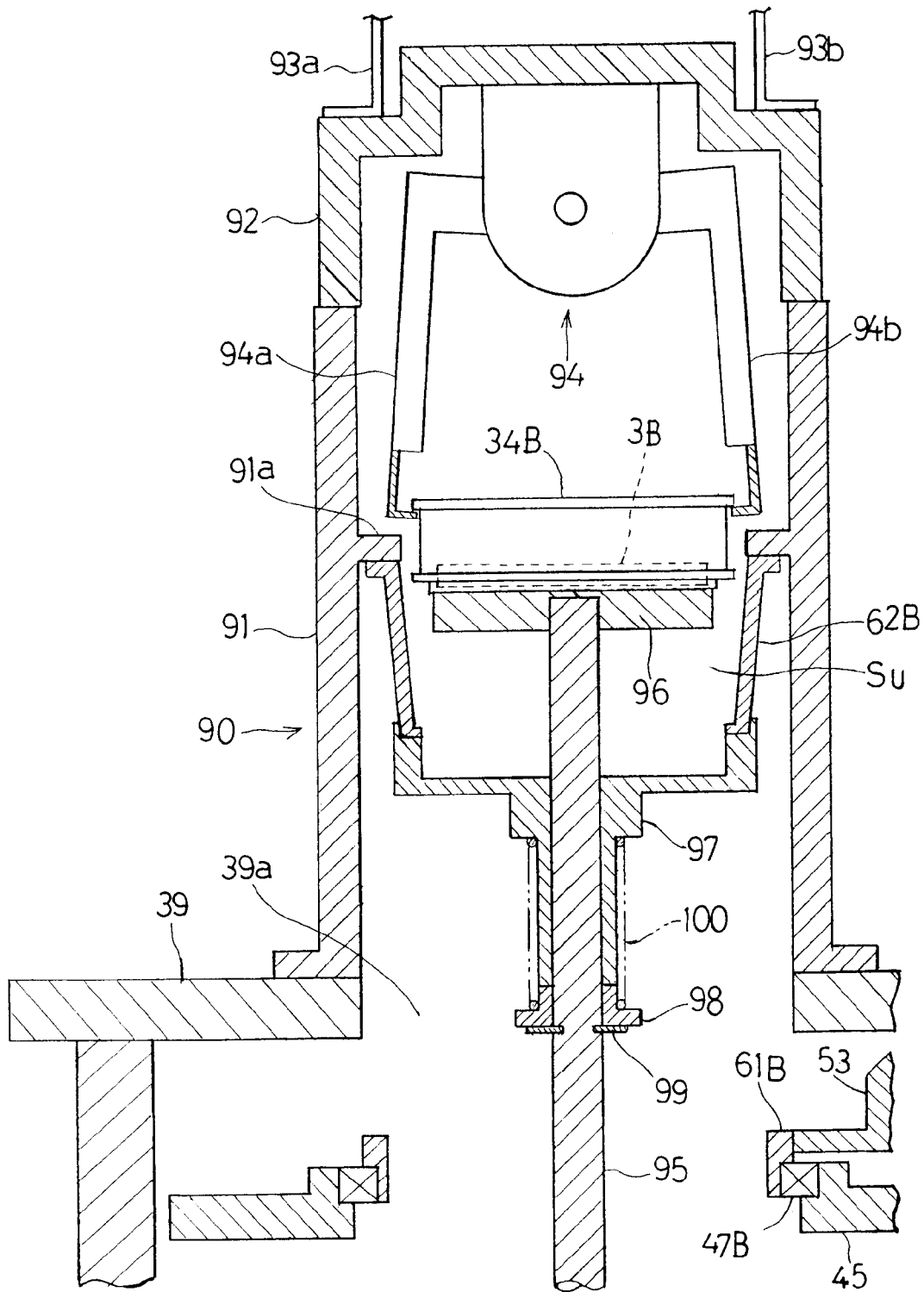
FIG. 6 is a longitudinal sectional view showing the sample replacement mechanism employed in the X-ray fluorescence spectrometer shown in FIG. 3 in another operation.

An atmospheric air is then introduced into the space $S_U$ to equalize the pressure inside the space $S_U$ to the atmospheric pressure and, as shown in FIG. 6, the holder table 96, with the sample holder 34B placed thereon, and the replacement shaft 95 are further elevated against the biasing force of the coil spring 100 with the coil spring 100 consequently compressed. The gripper 94 (FIG. 5) then held at a standby position with the gripper pawls 94a and 94b opened relative to each other is activated to close the gripper pawls 94a and 94b to engage an upper step of the sample holder 34B to thereby grip the sample holder 34B. While the gripper 94 holds the sample holder 34B in the manner described above, the cap 92 is subsequently shifted in the vertical direction and also in the horizontal direction by the shifting mechanism, followed by opening of the gripper pawls 94a and 94b of the gripper 94 to release the sample holder 34B at the standby position (not shown) where it had been held initially.

Following the procedure converse to that described above in connection with return of the sample holder 34B back to the standby position, the sample holder 34C having mounted thereon a sample 3C to be analyzed subsequent to the sample 3A (FIG. 3) currently held at the irradiating position is moved from the standby position to the position where the sample holder 34B occupies as shown in FIG. 5. It is to be noted that the sample holders 34 are placed at the respective standby positions (when placing, the sample holders 34 are held at predetermined rotating positions in the θ direction) after the desired target area (which may be in a plural number) of the placed sample 3 has been specified in the coordinate system with the center of the surface of the sample 3 taken as the point of origin. Also, after the cap 92 has tightly closed the upper end of the replacement shroud 91, the space $S_U$ is evacuated.

During the replacement of the sample performed in the manner described above, the interior of the chamber 39 is kept evacuated, and the stage 45 is rotatable in the circumferential direction r to such an extent that the wheel-shaped gear 61B will not interfere the replacement shaft 95 and the spring seat 98. In other words, while the sample is replaced at the delivery position, analysis can be concurrently performed at the irradiating position in the following manner. In the first place, the control means causes the r drive motor 40 of the r drive means 37 and the θ drive motor 50 of the θ drive means 38 to rotate properly to position the target area in the circumferential direction r and, also, in the $θ_A$ direction so that the primary X-rays 2 emitted from the X-ray source 1 can impinge upon the specified target area of the sample 3A and the secondary X-rays 5 emanating from the irradiated target area of the sample 3A can be received by the detecting means 6. The intensity of the secondary X-rays 5 emitted from the target area as a result of irradiation with the primary X-rays 2 is then measured by the detecting means 6 to thereby accomplish the fluorescent X-ray analysis. Where the plural target areas are specified, positioning and intensity measurement are sequentially performed to achieve the distributive analysis.

If averaged data are desired while a problem associated with non-uniformity of the sample is avoided, it is possible to achieve analysis of a round-shaped or ring-shaped large target area by utilizing the spinning function of the θ drive means 38 to continuously rotate the sample holder 34A at the irradiating position without any positioning as described above being performed. It is, however, to be noted that if the holder receptacle 48A is rotated at the irradiating position by rotating the θ drive shaft 53, the wheel-shaped gear 61B adjacent the delivery position will simultaneously rotate idle in a condition as shown in FIG. 5, but this poses no problem.

After the measurement of the intensity with respect to the sample 3A has been completely finished, the control means causes the r drive motor 40 of the r drive means 37 to rotate properly to thereby return the sample holder 34A to the position where it had occupied prior to the positioning, that is, the previously described reference position of the irradiating position. In this way, as shown in FIG. 5, the wheel-shaped gear 61B is held strictly at a position immediately below the sample holder 34C and the holder receptacle body 62B. Then, the holder table 96 on which the sample holder 34C and the holder receptacle body 62B are placed, the holder receptacle support 97 and the replacement shaft 95 are lowered with the sample holder 34C consequently brought to the delivery position as shown in FIG. 3. Thus, a cycle of replacement from the sample 3B to the sample 3C at the delivery position completes.

Subsequently, the control means causes the r drive motor 40 of the r drive means 37 to rotate 180° to thereby move the sample holder 34A at the irradiating position towards the delivery position and, at the same time, move the sample holder 34C at the delivery position towards the irradiating position, and the foregoing procedure is thereafter repeated. Unless no sample 3C to be subsequently analyzed is available, the sample holder 34A having mounted thereon the sample 3A which has already been analyzed is returned to the standby position in the manner described hereinbefore, thereby completing the analytical work.

As described hereinbefore, even with the spectrometer according to the second embodiment, the r drive means 37 drives the r drive shaft 43 to achieve both the transport function of transporting the sample 3 and the positioning function of positioning the target area in the r direction. Also, the θ drive shaft 53 of the θ drive means 38 that performs the positioning function of positioning the target area in the θ direction and the r drive shaft 43 of the r drive means 37 are positioned coaxially one inside the other to thereby form the dual coaxial shaft. Accordingly, the spectrometer can be assembled compact in size, resulting in reduction in cost. Also, as is the case with the θ stage employed in the conventional spectrometer, the θ drive means 38 has a spinning function of continuously rotating the sample 3 at the irradiating position.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. An X-ray fluorescence spectrometer for measuring an intensity of secondary X-rays emitted from a sample as a result of excitation with primary X-rays, said spectrometer comprising:

an r drive means for driving an r drive shaft to transport a sample holder in a circumferential direction about the r drive shaft between an irradiating position, at which the sample mounted in a sample holder is irradiated with the primary X-rays, and a delivery position at which replacement of the sample holder takes place and, also, for driving the r drive shaft at the irradiating position to thereby position a target area to be analyzed of the sample in the circumferential direction; and a θ drive means having a function of driving a θ drive shaft at the irradiating position to continuously rotating the sample holder about a center axis thereof and operable to drive the θ drive shaft at the irradiating position to position the target area of the sample about the center axis;

wherein the r drive shaft and the θ drive shaft form a dual coaxial shaft assembly.

2. The X-ray fluorescence spectrometer as claimed in claim 1, further comprising a stage coupled with the r drive shaft, a single sample holder being placed on the stage.

3. The X-ray fluorescence spectrometer as claimed in claim 1, further comprising a stage coupled with the r drive shaft, two sample holders are placed on the stage spaced 180° from each other in the circumferential direction, and wherein when one of the sample holder is held at the delivery position, the other of the sample holder is held at the irradiating position.

4. The X-ray fluorescence spectrometer as claimed in claim 3, wherein as the one of the sample holders is replaced at the delivery position, the target area of the sample mounted in the other of the sample holder is positioned in the circumferential direction and also about the center axis and is then irradiated with the primary X-rays.

* * * * *